United States Patent
Hübner et al.

(10) Patent No.: US 7,803,318 B2
(45) Date of Patent: Sep. 28, 2010

(54) HAND-HELD ANALYTICAL DEVICE

(75) Inventors: Ute Hübner, Lorsch (DE); Stephan Michael Frey, Frankfurt (DE); Michael Schabbach, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1016 days.

(21) Appl. No.: 11/019,046

(22) Filed: Dec. 21, 2004

(65) Prior Publication Data

US 2005/0187444 A1    Aug. 25, 2005

(30) Foreign Application Priority Data

Dec. 23, 2003 (DE) .............................. 103 60 786

(51) Int. Cl.
G01N 21/00 (2006.01)
A61B 5/00 (2006.01)

(52) U.S. Cl. ..................... 422/58; 422/63; 600/300; 600/322; 600/583

(58) Field of Classification Search .................... 422/58, 422/63; 600/300, 322, 583
See application file for complete search history.

(56) References Cited

U.S. PATENT DOCUMENTS

| | | | |
|---|---|---|---|
| 3,570,707 A * | 3/1971 | Finkel ............................ | 221/5 |
| 5,464,118 A | 11/1995 | Grau et al. | |
| 5,489,414 A | 2/1996 | Schreiber et al. | |
| 5,510,266 A | 4/1996 | Bonner et al. | |
| 5,575,403 A | 11/1996 | Charlton et al. | |
| 5,632,410 A | 5/1997 | Moulton et al. | |
| 6,379,317 B1 * | 4/2002 | Kintzig et al. .............. | 600/573 |
| 6,475,436 B1 * | 11/2002 | Schabbach et al. ............ | 422/64 |
| 6,497,845 B1 | 12/2002 | Sacherer | |
| 2002/0057993 A1 | 5/2002 | Maisey et al. | |
| 2002/0104849 A1 | 8/2002 | Giruad | |
| 2005/0090850 A1 * | 4/2005 | Thoes et al. ................. | 606/182 |

FOREIGN PATENT DOCUMENTS

| | | |
|---|---|---|
| EP | 0 732 590 A | 9/1996 |
| EP | 0 738 666 A | 10/1996 |
| EP | 0742436 A2 | 11/1996 |
| EP | 1022565 A2 | 7/2000 |
| JP | 60057259 | 4/1985 |

(Continued)

OTHER PUBLICATIONS

Translation of corresponding JP Office Action dated Dec. 19, 2006.

(Continued)

*Primary Examiner*—Lore Jarrett
(74) *Attorney, Agent, or Firm*—Bose McKinney & Evans LLP (57) ABSTRACT

The invention relates to a portable hand-held analytical device for analysis of a medically significant component of a sample, the device including a housing having a loading opening for receiving a replaceable drum cartridge containing analytical consumables, whereby the housing comprises on an outer side a dispensing opening through which the consumables can be pushed by means of a removal facility. The device includes a loading opening which is closeable by means of a lid, which upon closing effects a linear motion of a pushing part which moves the drum cartridge to a working position, in which it can be rotated about its geometric longitudinal axis.

21 Claims, 7 Drawing Sheets

FOREIGN PATENT DOCUMENTS

| | | |
|---|---|---|
| JP | 8285858 | 11/1996 |
| JP | 8304405 | 11/1996 |
| JP | 2002-196003 | 7/2002 |
| WO | 97/46887 A1 | 12/1997 |

OTHER PUBLICATIONS

Accu-Chek® Compact Blood Glucose System Reference Manual. Publ. Nr. 03307689001 (Aug. 2002) Roche Diagnostics, Mannheim, 2002.

* cited by examiner

HAND-HELD ANALYTICAL DEVICE

REFERENCE TO RELATED APPLICATIONS

This application claims priority to German Patent Application No. 103 60 786.2, filed Dec. 23, 2003, which is hereby incorporated by reference in its entirety.

BACKGROUND OF THE INVENTION

1. Field of the Invention

The invention relates to the field of portable hand-held analytical devices for analysis of medically significant components of samples, in particular biological fluids, comprising analytical measuring units, which receive replaceable drum cartridges, which can contain analytical consumables, in particular test strips.

2. Description of Related Art

Support-bound rapid tests have become established for chemical and biochemical analysis of solid and liquid sample materials in specialized laboratories and also, in particular, for the use outside of stationary laboratories. Based on a special-developed dry chemistry, these support-bound rapid tests can be performed easily and without complications even by untrained individuals despite the often complex reactions involving sensitive reagents.

A known example of support-bound rapid tests are test elements for the determination of the blood glucose level of diabetics. Diagnostic test elements provided in the form of strips are also called test strips. Known embodiments thereof include single- or multiple-field test strips for urine analysis and various indicator papers. Since support-bound tests also exist in a variety of shapes other than test strips, they are more generally denoted as "analytical consumables".

Such analytical consumables are packaged in a storage container in order to protect them from detrimental environmental influences, e.g. light, moisture or mechanical impact, and store them under sterile conditions. Aside from test strips, analytical consumables include for example lancets and sampling elements.

Since analytical consumables of this type have been described comprehensively in the prior art and a variety of embodiments thereof are known to experts in the field, no detailed description shall be provided herein. The analytical consumables are stored in a drum cartridge for example of the type described in European Patent Application No. 1 022 565 A2.

Portable hand-held analytical devices for analysis of a biological fluid, such as for example devices for the determination of blood glucose levels, are commonly used by individuals whose manual dexterity is impaired due to illness or age. For this reason, it is important for such analytical devices to be as easy as possible to operate with operating errors being largely excluded. A critical point in this context has proven to be the insertion or replacement of a drum cartridge in the analytical device. On the one hand, it is necessary to ensure exact positioning of the drum cartridge to ensure that the analytical consumables contained in the drum cartridge can reliably interact with the analytical sensor of the analytical device; on the other hand, the replacement of a drum cartridge must require no more than a low level of manual dexterity from the user of the analytical device.

Commonly marketed hand-held analytical devices are of a structure as described for example in U.S. Pat. No. 5,632,410 and U.S. Pat. No. 5,510,266. In an analytical device of this type, the drum cartridge is borne on an axis which extends through the entire length of the drum cartridge. This arrangement provides for sufficient positioning of the drum cartridge. However, it is also associated with the disadvantage of the drum cartridge being difficult to replace, since the axis must be pushed through a central bore hole of the drum cartridge which requires a considerable level of manual dexterity.

Moreover, Accu-Check® Compact™ blood glucose monitoring systems (Reference Manual. Publ. No. 03307689001 (08/02), Roche Diagnostics, Mannheim, 2002) are known from prior public use. These monitoring devices comprise a loading opening for receiving a drum cartridge which opening can be closed by a lid. An axis is situated in the loading opening onto which the drum cartridge can be slipped. The lid is closed by a swiveling motion and, in its closed state, presses onto the front side of the drum cartridge fixing the drum cartridge in its working position. However, for some measurements, a more precise axial positioning is desirable. Also, the drum cartridge can drop from the device upon opening of the loading opening causing further inconvenience.

BRIEF SUMMARY OF THE INVENTION

It is against the above background that the present invention proves certain unobvious advantages and advancements over the prior art. In particular, the inventor has recognized a need for improvements in hand-held analytical devices.

The present invention provides a way of simplifying the handling of a portable hand-held analytical device, in particular replacement of a corresponding drum cartridge containing analytical consumables, and simultaneously achieving correct positioning of the drum cartridge in the hand-held analytical device such that consumables of the drum cartridge can interact with the analytical measuring unit of the hand-held analytical device.

Closing of the device's lid effects a linear motion of a pushing part, which moves the drum cartridge to a working position, in which it can be rotated about its geometric longitudinal axis.

Advantageously, the positioning of the drum cartridge in its working position and the closing of the lid is combined in the hand-held analytical device according to the invention into a single handling step. A user of the hand-held analytical device according to the invention need not correctly position the drum cartridge, but the user rather inserts the drum cartridge, which can be done without precise positioning or exact adjustment of parts, and then simply closes the loading opening of the hand-held analytical device with the lid, whereby the drum cartridge is positioned. This can be done without any difficulty even by frail individuals whose manual dexterity is severely impaired.

Another advantage of a hand-held analytical device according to the invention is that the pushing part provides for exact and reliable axial and radial positioning of the drum cartridge. As a result, the analytical measuring unit can reliably interact with the analytical consumables contained in the drum cartridge.

In particular, the axial positioning of the drum cartridge can be performed in a hand-held analytical device according to the invention with sufficiently high precision for a code attached to the drum cartridge, e.g. a bar code, to be reliably readable with a code reader—which is preferred. By this means, for example a batch code of a drum cartridge can be read and information concerning the consumables contained therein can be taken into consideration in the analysis. An incorrectly read code may give rise to a false analytical result. For this reason, the distance-sensitive code reader must function very reliably, which requires precise positioning of the drum cartridge such as is afforded in an analytical device according to the invention. In particular, in an analytical device according to the invention, the code reader and its electrical connections can be arranged in a fixed place inside the housing of the analytical device. It is advantageous that the lid can be kept free from all components of the code reader, which simplifies the structure of the code reader and reduces its susceptibility to failure.

By means of the pushing part, it is possible to dispense with the axis extending through the drum cartridge and still achieve precise positioning by bearing the drum cartridge on its opposite ends in connection with the pushing part acting as the positioning facility. In particular, the positioning facility, which preferably pushes the drum cartridge against the bearing, can be used to compensate for manufacturing allowances, which allows for cost-efficient manufacturing.

An analytical device according to the invention is portable and therefore comprises an integral power source such that it is independent of the main supply. It is preferable for the power source to be provided in the form of one or several commercially available batteries, but may be provided for example in the form of solar cells.

These and other features and advantages of the present invention will be more fully understood from the following detailed description of the invention taken together with the accompanying claims. It is noted that the scope of the invention is defined by the claims and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Further details and advantages of the invention are illustrated in the following on the basis of exemplary embodiments making reference to the enclosed figures. Identical and corresponding parts are identified by identical reference numbers. The features illustrated therein can be used individually or in combination in order to create preferred further embodiments of the invention. The following is depicted in the figures.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood, reference is made to the following examples, which are intended to illustrate the invention, but not limit the scope therof.

DETAILED DESCRIPTION

The following description of the preferred embodiments is merely exemplary in nature and is in no way intended to limit the invention or its application or uses.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

Figure 1:
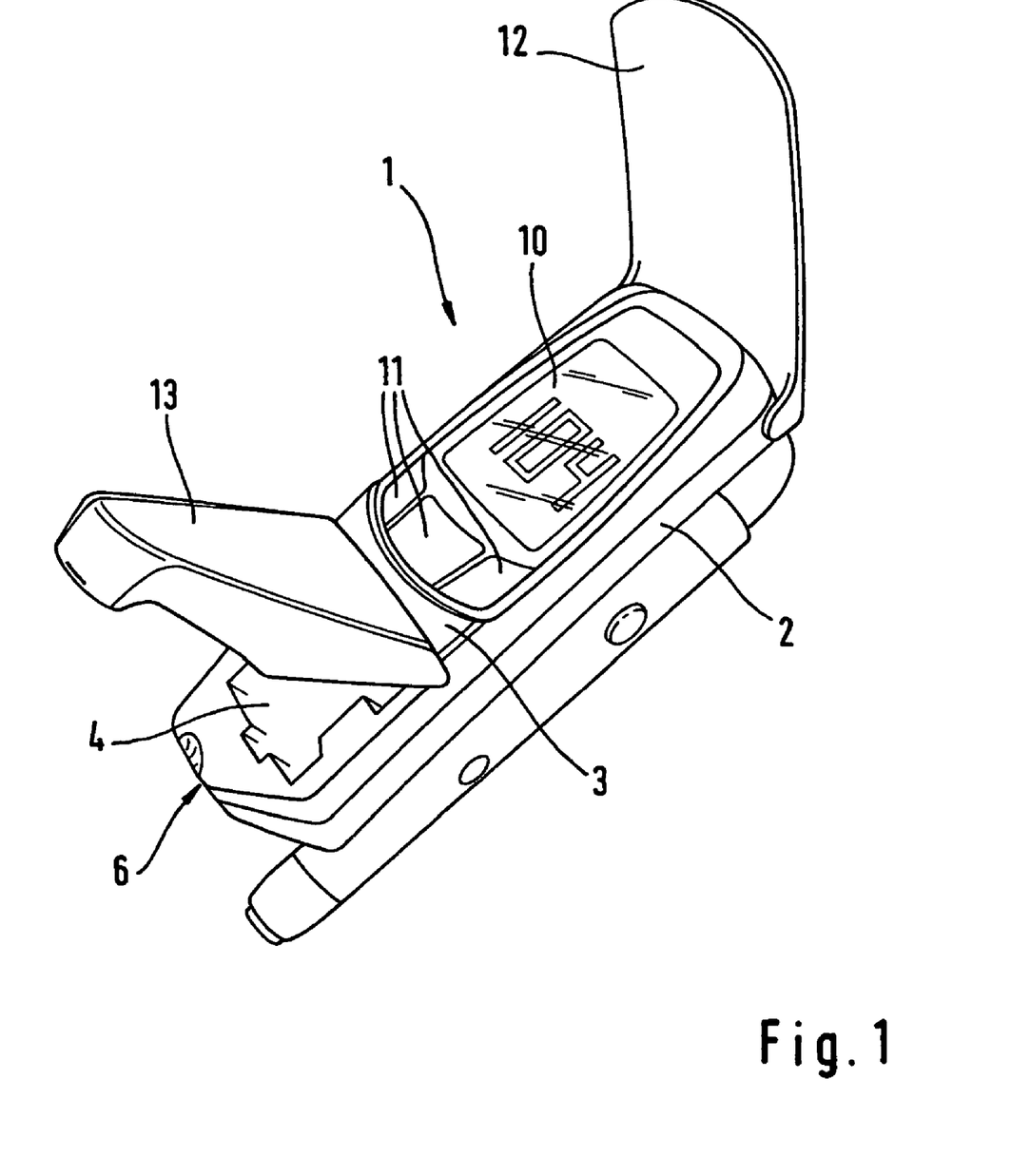
FIG. 1 shows an embodiment of a hand-held analytical device.

FIG. 1 shows an embodiment of an analytical device which is provided as a compact, portable hand-held analytical device 1 and serves for analysis of a medically significant component of a sample, in particular a biological fluid, such as for example blood, blood plasma, blood serum, urine, saliva, sperm, lymph fluid, synovial fluid, amniotic fluid, tear fluid, cystic fluid, sweat gland secretions or bile. The analytical device 1 comprises a housing 2 with a loading opening 4 in one longitudinal side 3 for receiving a replaceable drum cartridge 5.

Figure 3:
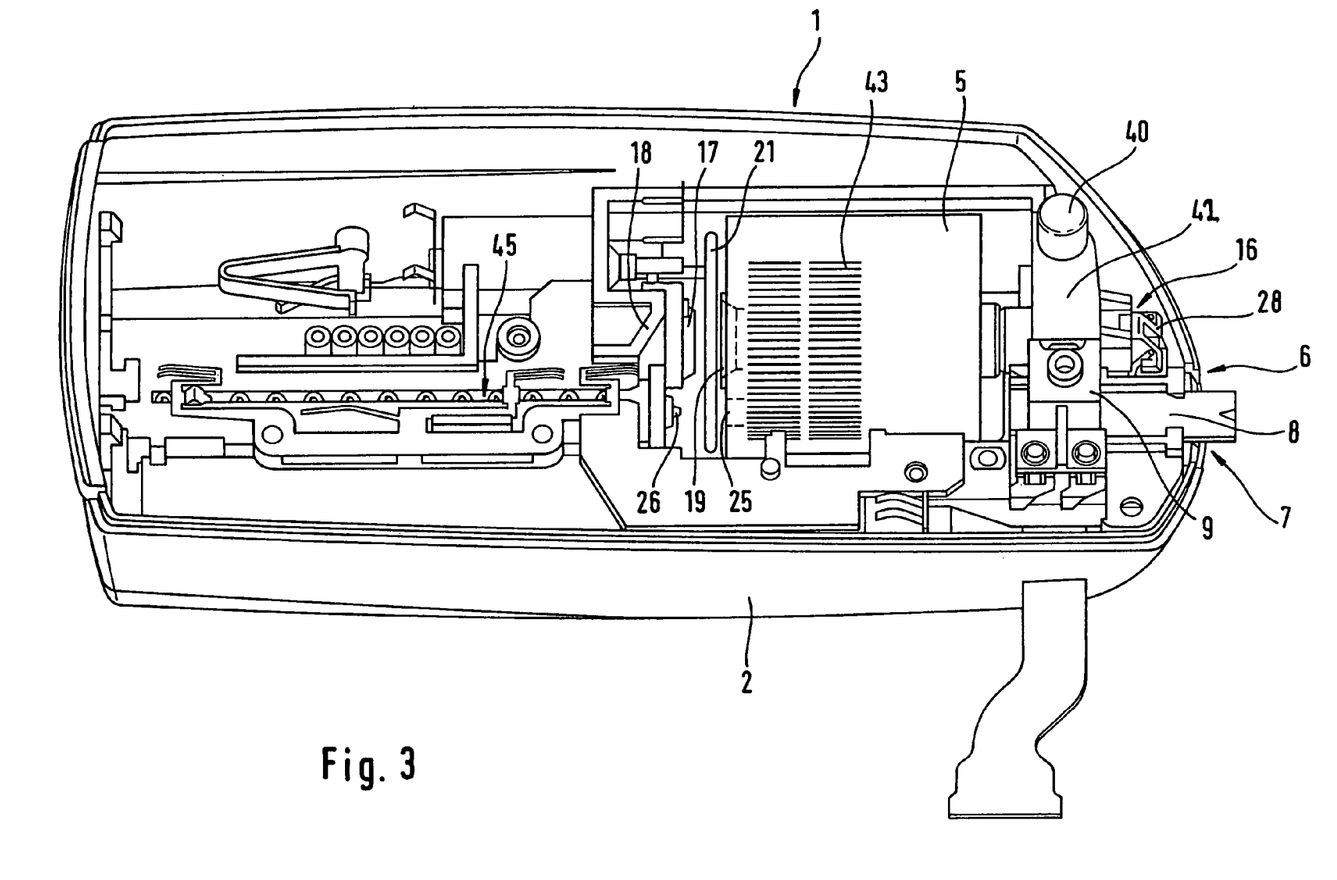
FIG. 3 shows the embodiment of FIG. 1 without the upper part of the housing.

The housing 2 comprises in an outer side, preferably in the front side 6, a dispensing opening 7 for analytical consumables 8 which are stored in the drum cartridge 5 (see FIG. 3). Preferably, these consumables 8 are provided in the form of test strips onto which for example a drop of blood can be placed. A reagent contained in the test strip then reacts with the medically significant component of the sample such that the result of the reaction can be analyzed with an analytical measuring unit 9 of the analytical device 1. An analytical measuring unit 9 of this type can for example be an optical sensor detecting a color change of a consumable 8, which is provided as a test strip, or an electronic sensor detecting a change in the conductivity of the sample.

The result of an analysis is displayed by means of a display facility 10, which preferably is a liquid crystal display. Adjacent to the display facility 10, keys 11 for operation of the analytical device 1 are arranged. A pivotable cover 12 can be attached to the housing 2 to serve as protection for these keys 11 and the display facility 10.

The loading opening 4 for receiving a drum cartridge 5 can be closed by a lid 13, which is pivotably attached to the housing 2.

The lid 13 shown in FIG. 2 comprises a positioning element 14 which shall be described in more detail in the following and is provided such that the drum cartridge 5 is pushed along its geometric longitudinal axis into its working position upon closing of the lid 13. Therefore, a swivel motion of the lid 13 is translated by the positioning element into a linear motion of the drum cartridge.

As is evident from FIG. 1, the lid 13 is attached to the housing 2 at its back end and the positioning element 14 is arranged at the front end of the lid 13. The positioning element 14 is provided in the form of a projection projecting into the inside of the housing 2 when the lid 13 is shut.

Figure 2:
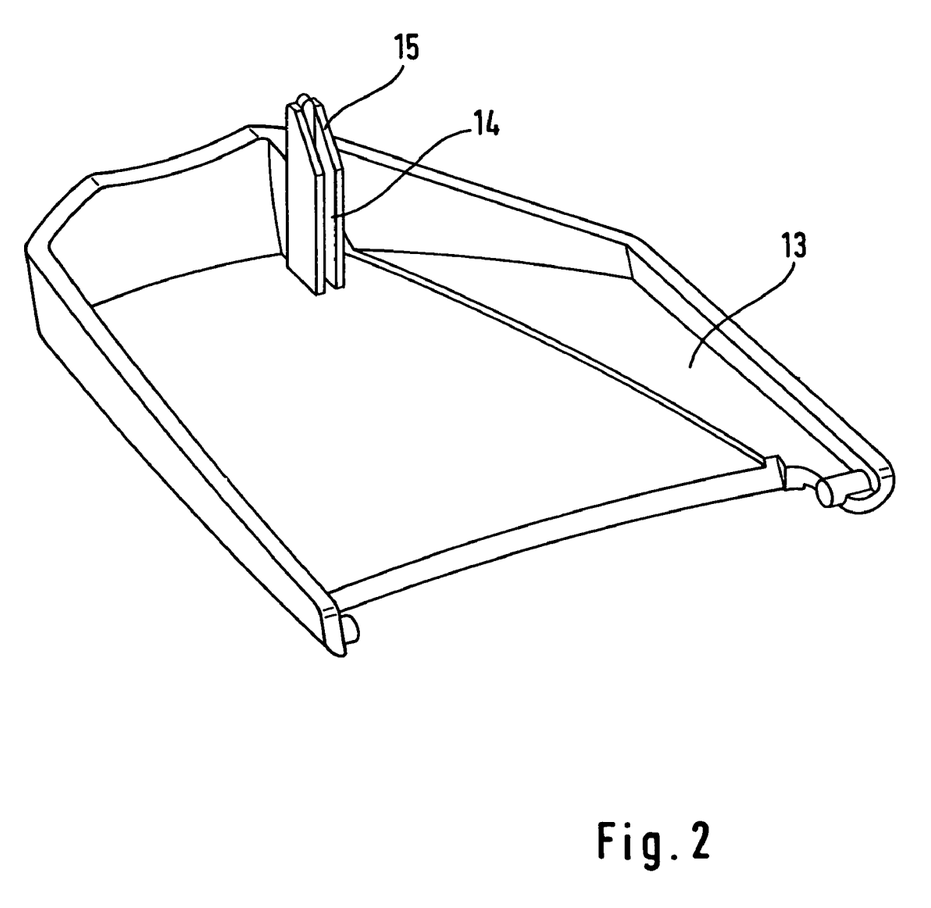
FIG. 2 shows the lid of the embodiment shown in FIG. 1.

As is particularly evident from FIG. 2, the positioning element 14 comprises an oblique surface 15. Upon closing of the lid 13, this oblique surface 15 touches on the positioning facility 16, which shall be described in more detail in the following, and presses against the positioning facility 16, whereby the swivel motion of the lid 13 is translated into a longitudinal motion of the positioning facility 16, i.e. in the direction of the geometric longitudinal axis of the drum cartridge 5. With the lid 13 being shut, the oblique surface 15 is at an angle to the geometric longitudinal axis of an inserted drum cartridge 5 and therefore also to the direction, in which the drum cartridge 5 is pushed upon closing of the lid 13, and faces an inserted drum cartridge 5.

FIG. 3 shows the analytical device 1 with the upper part of the housing removed such that the positioning facility 16 and the drum cartridge 5 can be seen in their working positions. In its working position, the positioning facility 16 presses the drum cartridge 5 against the bearing 17, which bearing 17 facilitates a rotation of the drum cartridge 5 about its geometric longitudinal axis. Alternatively, it is also possible that the positioning facility 16 holds the drum cartridge 5 in its working position without applying a pressing force. The bearing 17 comprises a carrier which engages an axial recess 19 on a front face of the drum cartridge 5 and supports the positioning thereof. An electrical motor 20 can be used to put in motion the drum cartridge 5 by means of the drum wheel 21 touching on its front face. Alternatively, it is also possible to put the drum cartridge 5 into rotation by means of a roller engaging its jacket surface. Batteries or storage batteries serve as the power source 22 for the electrical motor 20. Alternatively for example solar cells can be included as power source 22.

The drum cartridge 5 has several chambers 23 which are arranged in the shape of a ring around its geometric longitudinal axis and can contain analytical consumables 8. By means of a step-wise rotation of the drum cartridge 5, the consumables 8 can be removed sequentially as needed from the corresponding chamber 23 of the drum cartridge 5. The number of chambers 23 can be chosen fairly freely. Usually, 10 to 100 chambers are useful, preferably 15 to 30 chambers 23 are provided. As is particularly evident from FIG. 4, each chamber 23 comprises a removal opening 24 for removing one consumable 8 and one insertion opening 25 opposite from the removal opening 24 for inserting a plunger 26 of a removal facility 45, such as described in European Patent Application No. 1 022 565 A2, for transporting the consumable 8. The insertion and the removal openings 24, 25 are closed with a protective film to protect the consumables 8. The plunger 26 can be used to push consumables 8 from the chambers 23 for their use, whereby the protective film is penetrated. Depending on the size and shape of the consumables 8, the drum cartridge 5 may be of elongated cylindrical shape or of disc-like shape.

The positioning facility 16 comprises a pushing part 27 which pushes the drum cartridge 5 into the working position shown in FIG. 3 upon closing of the lid 13. The pushing part 27 comprises an oblique surface 28 which the positioning element 14 engages upon closing of the lid 13. In the process, the oblique surface 15 of the positioning element 14 presses against the oblique surface 28 of the pushing part 27, whereby a swivel motion of the lid 13 is translated into a linear motion of the pushing part 27. The pushing part 27 then pushes the drum cartridge 5 along its longitudinal axis to the working position and presses it against bearing 17. This pushing of the drum cartridge 5 can be associated with a small rotation step of the drum cartridge if the pushing part is guided accordingly.

The pushing part 27 comprises a peg 29 which engages an axial recess 30 of the drum cartridge 5 and thus provides for axial positioning of the drum cartridge 5.

Figure 4:
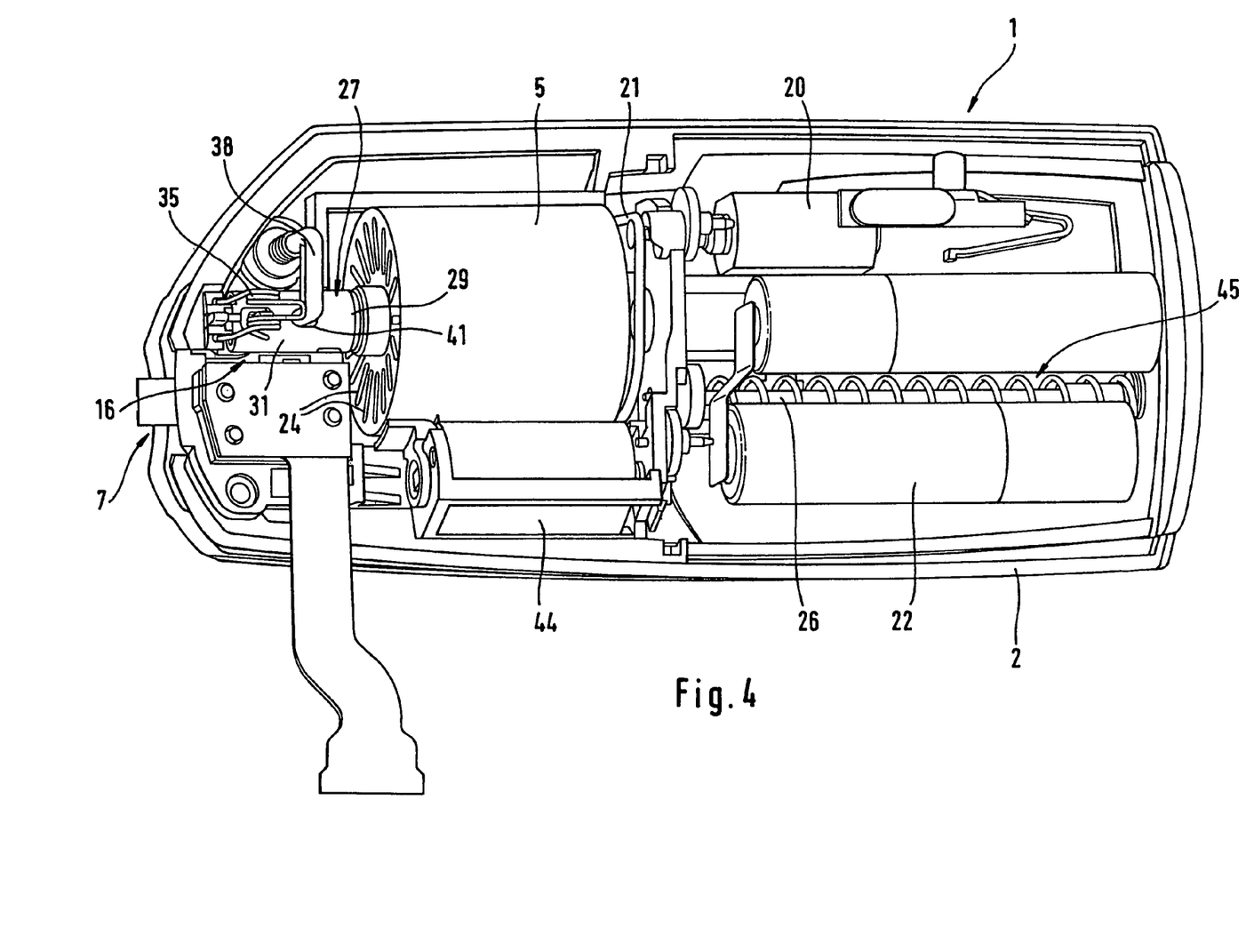
FIG. 4 shows a view from below of the embodiment of FIG. 1 without the housing.

FIG. 4 shows a view from below of the positioning facility 16 and the drum cartridge 5 with the housing 2 of the analytical device 1 removed. The pushing part 27 comprises an outer bushing 31 the front end of which provides the peg 29. In order to improve the exactly positioned engagement of the axial recess 30 of the drum cartridge 5 by peg 29, the peg 29 preferably comprises a bezel 32 or is provided to be conical in shape at its front, engaging end, which is particularly evident from FIG. 5.

Figure 5:
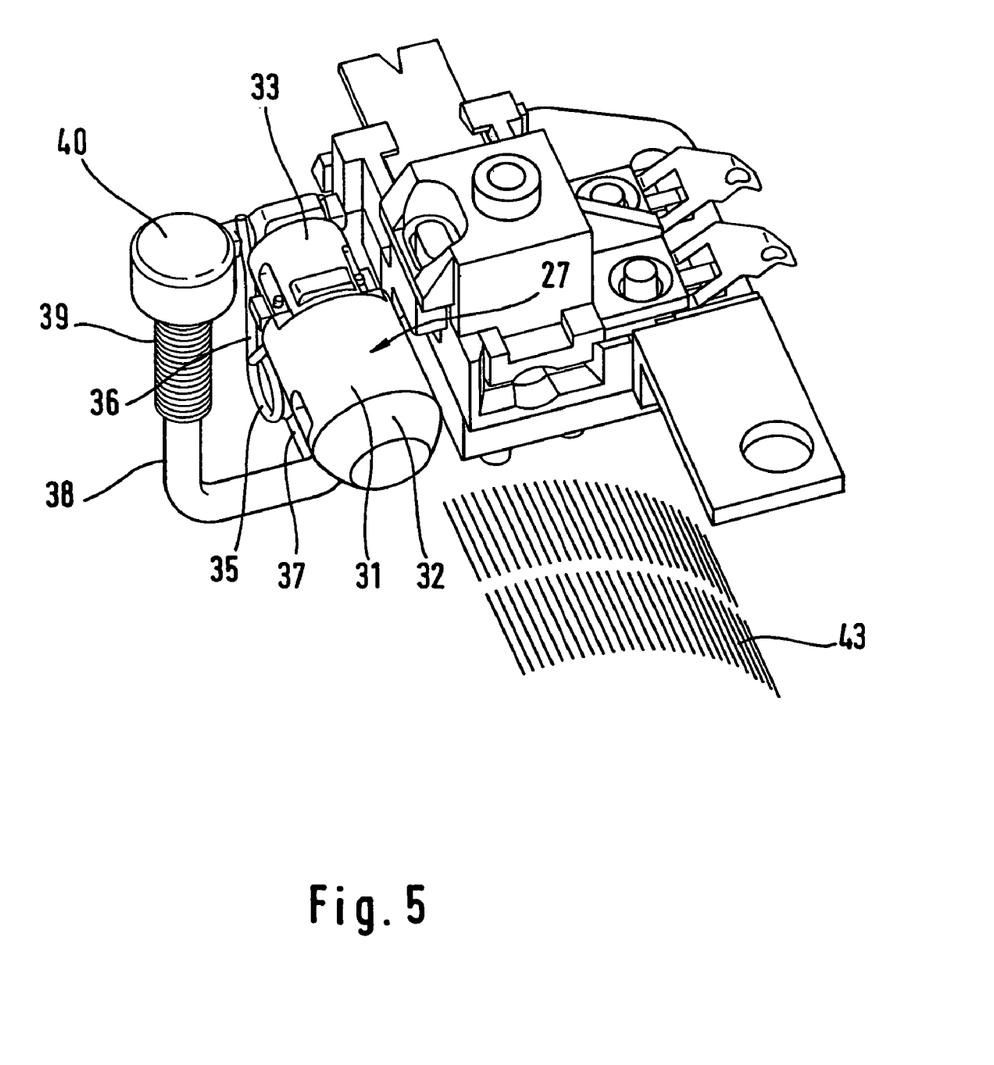
FIG. 5 shows the positioning facility of the embodiment of FIGS. 1 to 4.

FIG. 5 shows the positioning facility 16 in detail, whereby a part of the outer bushing 31 is removed such that the structure of the pushing part 27 can be seen better. A piston 32 with a helical spring 34 is situated inside the bushing 31 of the pushing part 27, whereby one end of the helical spring 34 presses against the outer bushing 31 and the other end presses against the piston 32. The piston can be moved with respect to the outer bushing 31 of the pushing part 27 such that the length of the pushing part 27 can be varied. The spring 34 is also arranged between the peg 29 and the oblique surface 28. The spring 34 can be used to compensate for manufacturing allowances in axial direction. On its end facing away from the outer bushing 31 the piston 32 comprises the above-mentioned oblique surface 28 of the positioning facility 16 which interacts with the positioning element 14 which is attached to the lid 13.

As is particularly evident from FIG. 5, the positioning facility 16 comprises a second spring 35 which is provided in the form of a leg spring. The second spring 35 is supported to be fixed in place with respect to the housing 2 and presses against the positioning element 14 such that the pushing part 27 is reset upon opening of the lid and the drum cartridge 5 can be removed. The second spring 35 comprises a first leg 36 which it uses to press against the pushing part 27. The spring 35 supports itself with a second leg 37 in a fixed place with respect to the housing 2.

In order to reduce the pressure in the longitudinal direction of drum cartridge 5 exerted by the two springs 34, 35 on the positioning element 14, which is arranged on lid 13, a fixing element 38 is provided which allows the pushing part 27 to be fixed in the position shown in FIG. 3. In particular, this fixing element 38 also prevents the pushing part 27 or the drum cartridge 5 from being propelled uncontrolled from the loading opening 4 of the analytical device 1 upon opening of the lid 13. The pushing part 27 can be fixed in place by means of the fixing element 38 after it moved the drum cartridge 5 to its working position shown in FIG. 3.

It is preferable for the fixing element 38 to engage the pushing part 27 in a positive lock-type fashion, since positive locking is typically a more reliable type of securing as compared to the also feasible frictional connection. As is particularly evident from FIG. 5, the fixing element 38 is mounted on a spring bearing by means of spring 39 and arranged in a U-shape around the pushing part. By manually pressing onto one end of the fixing element 38, which is provided with a button 40 for improved handling in the embodiment shown, the other end of the fixing element 38 is lifted off the pushing part 27 and thus loosened from its engagement with a lock-in position 41 of the pushing part 27.

Provided in the form of a helical spring, spring 39 is arranged around the fixing element 38 and abuts on carrier fin 42 and thus presses the fixing element 38 against the pushing part 27.

The lock-in position 41 of the pushing part 27 is provided in the form of a pocket hole. When, upon closing of the lid 13, the lock-in position 41 of the pushing part 27 is pushed past the fixing element 38, the fixing element 38 is pressed into the lock-in position 41 by spring 39 such that a positive lock is generated.

As is particularly evident from FIG. 3, the drum cartridge 5 can comprise a bar code 43. If the consumables 8 are provided, for example, in the form of test strips for determining the blood glucose level, a batch code contained in the bar code can be taken into consideration during the analysis of the color signal generated by the test strip. A bar code reader 44, being fixed in place with respect to the housing, can automatically read the bar code 43 upon insertion of a new drum cartridge 5 such that information contained therein can be taken into consideration in the analysis of a measuring result. This is advantageous in that the measuring accuracy can be improved without having to enter this information by hand. The precise positioning of a drum cartridge 5 in the analytical device 1 described above provides the advantage of being able to use distance-sensitive bar code readers 44 without any concerns about reading errors.

Figure 6:
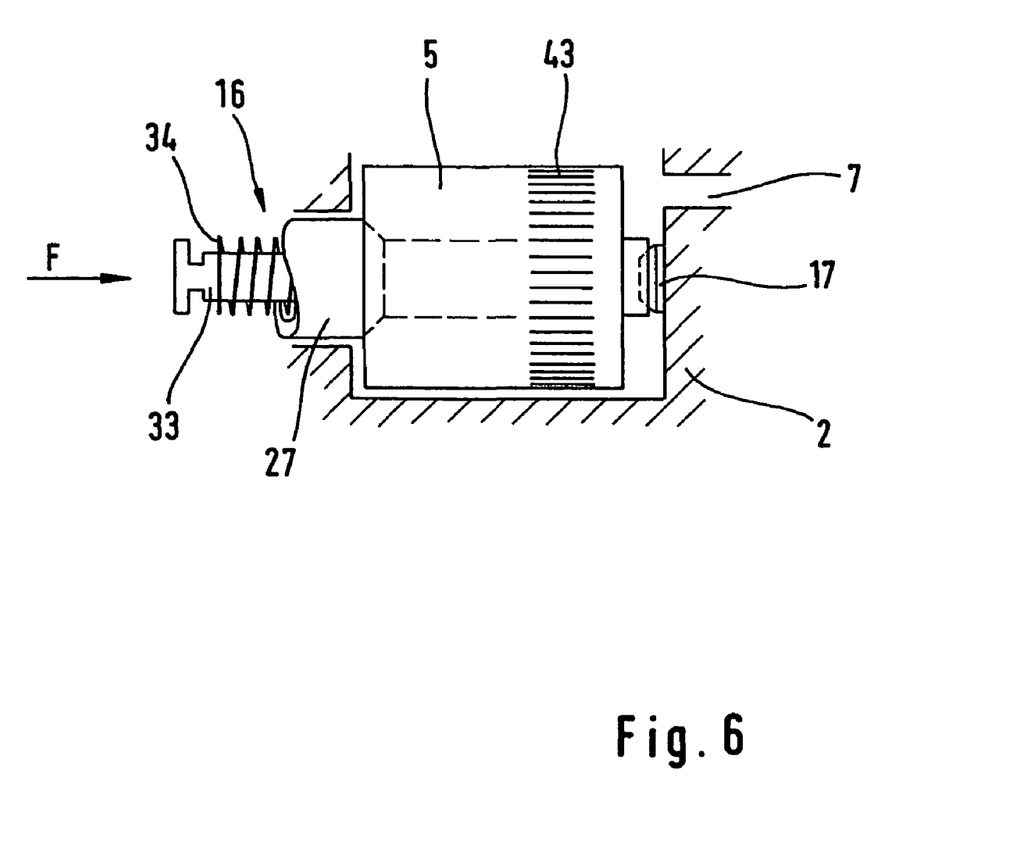
FIG. 6 shows another embodiment of the positioning facility.

In the embodiment described with reference to FIGS. 1 through 5, the drum cartridge 5 is pushed backwards from the dispensing opening 7 of the analytical device 1 onto the fixed carrier 18 of the bearing 17 upon closing of the lid 13. The leg spring 35 is put under pressure upon closing of the lid 13 and relaxes upon opening of the lid 13. However, this structure is not obligatory. It is just as feasible for the drum cartridge 5, upon closing of the lid 13, to be pushed towards the front face 6 of the analytical device 1 bearing the dispensing opening 7, as is shown in FIG. 6. In an alternative structure of this type, the pushing part 27 and the carrier 18 of the bearing 17 with the drum wheel 21 for driving the drum cartridge 5 are arranged on the correspondingly other side as compared to the embodiment described in FIGS. 1 to 5.

In the embodiment shown in FIG. 6, the spring 35 is arranged such that a tensile force is applied to it upon opening of the lid 13, for example by means of the positioning element 14 engaging and pulling the pushing part 27. Upon closing of the lid 13, the spring 35 then retracts the pushing part 27 such that the drum cartridge 5 is held in its working position.

Figure 7:
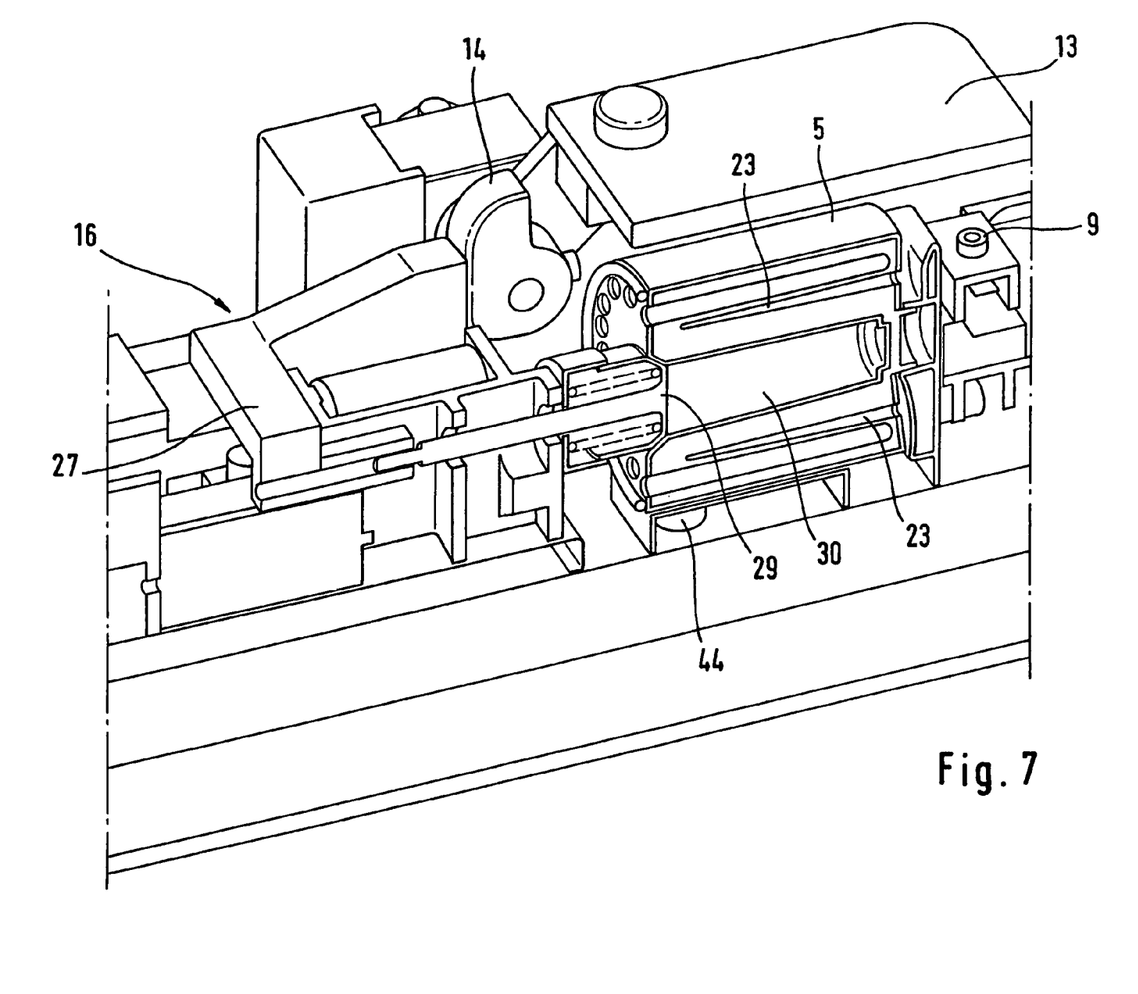
FIG. 7 shows another embodiment of the positioning facility.

FIG. 7 shows in detail how to implement the alternative structure described by means of FIG. 6, in which the drum cartridge 5 is pushed towards the dispensing opening 7 upon closing of the lid 13. In the embodiment shown in FIG. 7 with the drum cartridge 5 inserted and the lid 13 closed, the positioning element 14 is provided in the form of a cam plate attached to an extension arm of the lid 13 through which the lid 13 is connected in a hinged fashion to the housing 2 of the analytical device 1. The pushing part 27 is provided to be U-shaped and is pressed by spring force against the positioning element 14 provided in the form of a cam plate. In the process, one leg of the U-shaped pushing part 27 touches on the cam plate 14, whereas the other leg presses against the drum cartridge 5.

Opening of the lid 13 causes the cam plate 14 to rotate. Thereby, the non-spherical shape of the outer surface of the cam plate 14 causes the pushing part 27 to be pressed backwards against the spring force, i.e. away from the dispensing opening 7. In the process, the pushing part 27 disengages from the axial recess 30 of the drum cartridge 5 such that it can be removed from the opened analytical device 1 and a new drum cartridge 5 can be inserted. When the lid 13 is then closed again, the cam plate 14 re-assumes the position shown in FIG. 7 and the pushing part 27 can be moved forward by spring force. In the process, one of the legs of the U-shaped pushing part 27 is made to engage the drum cartridge 5 and push it into its working position.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A portable hand-held analytical device for analysis of a medically significant component of a sample, said device comprising:
    an analytical measuring unit,
    a housing comprising a loading opening for receiving a replaceable drum cartridge, which can comprise analytical consumables and comprises at least one removal opening adapted to be disposed at a front face of the drum cartridge,
    a pushing part movably disposed in the housing and operable to contact and push a drum cartridge into a working position, the pushing part comprising a spring,
    a lid for closing the loading opening, the lid comprising a positioning element that projects into the inside of the housing when the lid is closed,
    a bearing for the drum cartridge facilitating a rotation of the drum cartridge about the geometric longitudinal axis of the drum cartridge, and
    a removal facility for removing the analytical consumables from the drum cartridge, said housing comprising on one outer side a dispensing opening through which a consumable can be pushed by means of the removal facility, wherein
    closing the lid causes the positioning element to press against and effect a linear motion of the pushing part, the linear motion of the pushing part causing the pushing part to push the drum cartridge to a working position, in which it can be rotated about its geometric longitudinal axis.

2. The hand-held analytical device of claim 1, wherein the pushing part engages an axial recess of the drum cartridge.

3. The hand-held analytical device of claim 1 further comprising a fixing element by means of which the pushing part can be fixed in place.

4. The hand-held analytical device of claim 3 wherein the pushing part can be fixed in place such that it locks the drum cartridge in the working position in a rotatable position.

5. The hand-held analytical device of claim 3 wherein the pushing part comprises a lock-in position, which can engage the fixing element in a positive locking fashion.

6. The hand-held analytical device of claim 3 wherein the fixing element is borne on springs.

7. The hand-held analytical device of claim 3 wherein the fixing element is arranged in a U-shape around the pushing part such that by applying pressure to one end of the fixing element its other end can be loosened from engagement with the pushing part.

8. The hand-held analytical device of claim 1 wherein the pushing part can be pushed in the direction of the geometric longitudinal axis of an inserted drum cartridge.

9. The hand-held analytical device of claim 1 wherein the lid, upon closing, acts on the pushing part by means of a positioning element.

10. The hand-held analytical device of claim 1 wherein the lid is attached to the housing so as to be capable of swiveling.

11. The hand-held analytical device of claim 1 wherein the spring exerts a pressure in the longitudinal direction on the pushing part and compensates for manufacturing tolerances in the axial direction.

12. The hand-held analytical device of claim 11 wherein the spring is a helical spring.

13. The hand-held analytical device of claim 1 wherein the bearing comprises a carrier which engages an axial recess of the drum cartridge.

14. The hand-held analytical device of claim 1 further comprising a reader sensor for reading a code on the jacket surface of the drum cartridge, which reader sensor is arranged such that it is fixed in place inside the housing.

15. The hand-held analytical device of claim 1 wherein the loading opening is arranged in one longitudinal side of the housing.

16. A hand-held analytical device for analysis of a medically significant component of a sample, comprising:
   an analytical measuring unit;
   a housing comprising a dispensing opening and a loading opening, the loading opening configured to receive a replaceable drum cartridge having a removal opening through which an analytical consumable can move;
   a bearing for contacting one end of the drum cartridge, the bearing facilitating rotation of the drum cartridge about its longitudinal axis;
   a removal facility configured for moving the analytical consumable from the drum cartridge through the dispensing opening;
   a pushing part movably disposed in the housing and operable to contact and push a drum cartridge into a working position, the pushing part comprising a spring,
   a lid for closing the loading opening, the lid comprising a positioning element that projects into the inside of the housing when the lid is closed; and
   wherein closing the lid causes the positioning element to press against and produce a longitudinal movement of the pushing part, which in turn causes the pushing part to move the drum cartridge into a working position.

17. The hand-held analytical device of claim 16, wherein the lid swivels as it closes.

18. The hand-held analytical device of claim 17, wherein, the swivel of the lid is translated into axial movement of the drum cartridge.

19. The hand-held analytical device of claim 16, wherein the longitudinal movement of the pushing part is substantially along the longitudinal axis of the drum cartridge.

20. The hand-held analytical device of claim 16, wherein the pushing part engages a recess of the drum cartridge for axially positioning the drum cartridge in the working position.

21. The hand-held analytical device of claim 16, further comprising a fixing element for securing the pushing part in the housing, wherein as the lid is opened the fixing element prevents the pushing part and drum cartridge from being propelled through the loading opening.

* * * * *